United States Patent [19]
Girijavallabhan et al.

[11] Patent Number: 4,503,064
[45] Date of Patent: Mar. 5, 1985

[54] OXIME SUBSTITUTED PENEMS

[75] Inventors: Viyyoor M. Girijavallabhan, Parsippany; Ashit K. Ganguly, Upper Montclair; Patrick A. Pinto, Mine Hill; Richard W. Versace, Ringwood, all of N.J.

[73] Assignee: Schering Corporation, Kenilworth, N.J.

[21] Appl. No.: 576,499

[22] Filed: Feb. 2, 1984

Related U.S. Application Data

[63] Continuation-in-part of Ser. No. 445,295, Nov. 29, 1982.

[51] Int. Cl.³ ................. C07D 499/00; A61K 31/425

[52] U.S. Cl. .............................. 514/210; 260/245.2 R; 260/245.2 T; 260/239 A

[58] Field of Search ................. 260/245.2 T, 245.2 R, 260/239.1; 424/270, 271

[56] References Cited

U.S. PATENT DOCUMENTS 4,423,055 12/1983 McCombie ......................... 424/270

Primary Examiner—Nicholas S. Rizzo
Attorney, Agent, or Firm—Gerald S. Rosen

[57] ABSTRACT

There is disclosed 2-(oximinoalkylthio)penems and their pharmaceutically acceptable salts and esters and their use as antibacterials.

17 Claims, No Drawings

OXIME SUBSTITUTED PENEMS

RELATED APPLICATIONS

This application is a continuation-in-part of U.S. patent application Ser. No. 445,295 filed Nov. 29, 1982.

BACKGROUND OF THE INVENTION

This invention relates to 2-(oximinoalkylthio)penems and their pharmaceutically acceptable salts and esters, which compounds possess potent antibacterial activity.

There is a continuing need for new antibacterial agents because continued extensive use of effective antibacterials gives rise to resistant strains of pathogens.

SUMMARY OF THE INVENTION

The novel penem compounds of this invention are represented by the formula

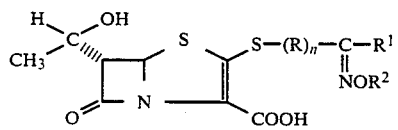

and pharmaceutically acceptable salts and pharmaceutically acceptable esters thereof, in racemic or optically active forms
wherein
n is one or two;
R represents

wherein $R^3$ and $R^4$ are independently selected from hydrogen, lower alkyl, hydroxy-lower alkyl, halo-lower alkyl, amino-lower alkyl, carbamido-lower alkyl, cyano-lower alkyl, carbamoyloxy-lower alkyl, carbamoyl-lower alkyl, carboxy-lower alkyl, heterocyclyl-lower alkyl wherein the heterocyclic moiety has 5 or 6 ring atoms, at least one of which is carbon, and the remaining 4 or 5 ring atoms are independently selected from carbon, nitrogen, oxygen and sulfur; or $R^3$ and $R^4$ taken together are =O;

$R^1$ represents hydrogen, lower alkyl, hydroxy-lower alkyl, amino-lower alkyl, carboxy-lower alkyl, carbamoyloxy-lower alkyl, carbamoyl-lower alkyl, halo-loweralkyl, cyano-lower alkyl, heterocyclyl lower alkyl wherein the heterocyclic moiety has 5 or 6 ring atoms, at least one of which is carbon, and the remaining ring atoms are independently selected from oxygen, carbon, nitrogen and sulfur;

$R^2$ represents hydrogen, lower alkyl, carboxy-loweralkyl, hydroxy-lower alkyl, cyano-lower alkyl, amino-lower alkyl, imidazolyl-lower alkyl, triazolyl-lower alkyl, tetrazolyl-lower alkyl or pyridinium-lower alkyl.

As used herein, the term "lower alkyl" means straight or branched chain alkyl groups of 1 to 6 carbon atoms, e.g. methyl, ethyl, propyl, iso-propyl, butyl, t-butyl, pentyl, neopentyl, hexyl and the like; "halo" means fluorine, chlorine, bromine or iodine with fluorine preferred; "heterocyclyl" means a heterocyclic group with 5 or 6 ring atoms, at least one of which is carbon, and the remaining 4 or 5 ring atoms are independently selected from carbon, nitrogen, oxygen and sulfur, the preferred heterocyclics contain a nitrogen bonded to the lower alkyl moiety.

Heterocyclic groups within the scope of this invention are, for example, pyrrole, imidazole, imidazolidine, pyrazole, triazole, isothiazole, pyridinium, tetrazole, thiadiazole, thiazole, and the like. All position isomers of the heterocyclics are contemplated for examples, 1,2,4-triazole, 4,1,2-triazole, 1,2,3-triazole, 2,1,3-triazole, 1,3-triazole, 1,2,3,4-tetrazole, 2,1,3,4-tetrazole and the like.

Preferred heterocyclics are imidazole, 1,2,4-triazole, 1,2,3-triazole 1,3-thiazole and imidazolidine.

Preferred compounds of formula I are those in which $R^1$ and $R^2$ are each independently hydrogen or lower alkyl; and $R^3$ and $R^4$ are each hydrogen.

The most preferred compounds are those in which n is one, $R^2$, $R^3$ and $R^4$ are each hydrogen and $R^1$ is either hydrogen or methyl.

"Pharmaceutically acceptable salts" as used herein means alkali metal salts such as sodium and potassium salts; alkaline earth metal salts such as calcium, magnesium and aluminum salts; amine salts formed from a wide variety of suitable organic amines, i.e., araliphatic, cycloaliphatic, (cycloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperidine. Acid addition salts formed from mineral acids such as hydrochloric, hydrobromic, hydroiodic, phosphoric or sulfuric acids, or formed from organic carboxylic or sulfonic acids such as trifluoroacetic, para-toluene sulfonic, maleic, acetic, citric, oxalic, succinic, benzoic, tartaric, fumaric, mandelic, ascorbic acid and malic acids. The compounds of this invention which contain a 3-carboxylic group and a basic group (the heterocyclic group) form an inner salt, i.e., a Zwitterion.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. Salts can be formed, for example, by treating with metal compounds such as alkali metal salts of suitable carboxylic acids, or with ammonia or a suitable organic amine, wherein preferably stoichiometric amounts or only a small-excess of the salt-forming agent is used. Acid addition salts are obtained in the usual manner, for example, by treating with an acid or a suitable anion exchange reagent. Inner salts of the compounds of formula I, i.e., a zwitterion, may be formed by neutralizing salts such as acid addition salts to the isoelectric point. The esters are preparable in a manner analogous to the preparation of the corresponding esters of penicillins and cephalosporins.

Salts may be converted in the usual manner into the free carboxy compounds.

Compounds of this invention possess 3 or more asymmetric carbon atoms indicated in the partial formula I(a) below at the 5, 6 and 8 and the 2′ and 3′-position carbon atoms

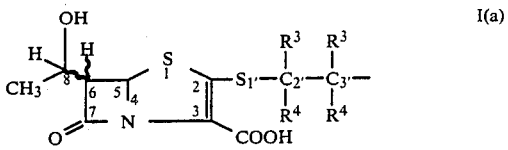

At the 5,6 and 8 positions, compounds of the invention may possess 5R, 6S, 8R or 5R, 6R, 8S stereochemistry at those chiral atoms. The preferred absolute stereochemistry for the compounds of the present invention at those positions is 5R, 6S, 8R.

Compounds of this invention wherein $R^3$ and $R^4$ on the carbon atom are different will have additional asymmetric carbon atom(s) as shown in formula I(a) at the 2′ and 3′ positions. All the possible resulting stereoisomers are included herein.

DETAILED DESCRIPTION

When tested in standardized microbiological assays, the compounds of this invention are active against such gram-positive organisms as *Staphylococcus epidermis* and *Bacillus subtilis,* and such gram-negative organisms as *E. coli* and Salmonella at test levels of 0.06 to 1.0 micrograms/ml. Additionally, they show activity against organisms which produce beta-lactamases, e.g., penicillinase and cephalosporinase, indicating a resistance against these enzymes.

The compounds of this invention exhibit low protein binding and their metabolites have little or no unpleasant odor.

As antibacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals including humans, having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g., transdermal. Parenteral administration is preferred.

Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants; ethylene glycol polymers; betacyclodextrin; fatty alcohols, hydrolyzed cereal solids; water; polyalkylene glycols; gums; and petroleum; as well as other non-toxic compatible fillers, binders, disintegrants and lubricants commonly used in pharmaceutical formulations. The compositions may also contain perservatives, aerosol propellants and coloring, thickening, suspending, dispensing, emulsifying, wetting, stabilizing and buffering agents.

The dosage of the compounds of this invention which is administered is dependent, in the judgement of the attending clinician, upon a variety of factors, i.e., the age and weight of the individual being treated, the mode of administration, the potency of the administered compound and the type and severity of the bacterial infection being prevented or reduced. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

The compounds of this invention are prepared by the processes disclosed in applicants assignees copending U.S. patent application Ser. No. 549,535 entitled "Process for the Production of Penems" filed Nov. 7, 1983. The processes disclosed therein are preferred over other known suitable processes for preparing penems.

The process designated as process A in the aforesaid patent application comprises:

(a) reaction of an azetidinone of the formula

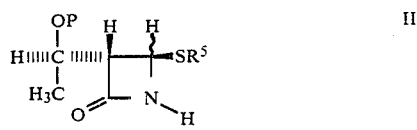

wherein P is a removable hydroxy protecting group or hydrogen; and $R^5$ is a sulfur protecting group selected from triphenylmethyl, diphenylmethyl, 2-pyranyl, or lower alkyl carbonyl; with a compound of the formula IIIa and IIIb.

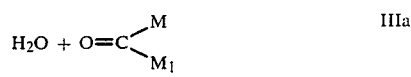

wherein M and $M_1$ are independently —COOCH$_2$CH$_2$R$^6$ or —COOCH$_2$CH=CH$_2$; R$^6$ is trimethylsilyl, t-butyldiphenylsilyl or other equivalently functioning lower alkylsilyl groups, cyano or a sulfone of the formula —SO$_2$—aryl; to form the intermediate of the formula IV

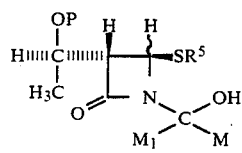

IV wherein P, R⁵, M and M₁ are as hereinabove defined;

(b) treatment of the compound of formula IV with chlorinating agent to form the following compound of formula V

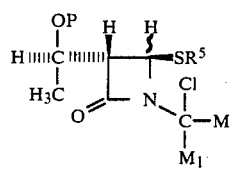

V wherein P, R⁵, M and M₁ are as defined hereinabove;

(c) treatment of the compound of formula V with a stoichiometric excess of elemental zinc in a strong acid such as hydrochloric acid to effect removal of the chlorine and the removable sulfur and hydroxy protecting groups, and, if a removable hydroxy protecting group is utilized which is not removable with zinc, subsequent removal of said hydroxy protecting group, producing a compound of formula VI

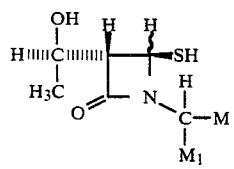

VI wherein M and M₁ are as hereinabove defined;

(d) treatment of the compound of formula VI with a hydroxy protecting group to form the compound of formula VI(a)

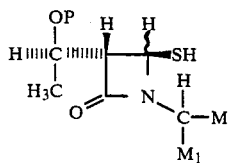

VI(a)

wherein M and M₁ are defined hereinabove and P is a hydroxy protecting group as defined hereinabove;

(e) reaction of the compound of formula VI or VI(a) with a thiocarbonyl compound of formula VII

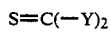

VII wherein Y is a leaving group; to form a compound of formula VIII

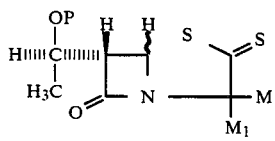

VIII wherein P, M and M₁ are as hereinabove defined;

(f) treatment of the compound of formula VIII wherein P is a hydroxy protecting group with an aqueous acid solution to deprotect the hydroxy group to form a compound of formula VIII(a)

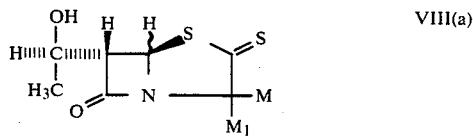

VIII(a)

wherein M and M₁ are as hereinabove, defined;

In an alternative procedure, compounds of formula VIII(a) can be prepared from compounds of formula V by eliminating steps (d) and (f) (i.e., the protection and subsequent deprotection of the hydroxyl group at the C-8 position).

(g) treatment of the compound of formula VIII(a) with a fluoride ion (where M is —COOCH₂CH₂R⁶ only one equivalent of fluoride is used) to form the compound of formula IX(a) which is tautomeric with formula IX(b)

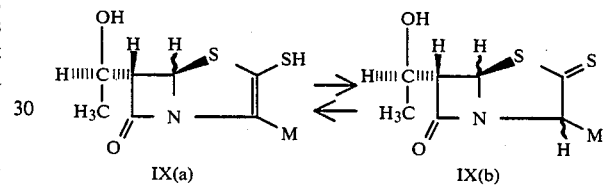

wherein M is as defined above.

(h) reaction of the tautomer of formulas IX(a) and IX(b) with a compound of formula XII

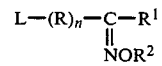

XII wherein L is a leaving group such as trifluoromethansulfonyl (triflate), bromine or chlorine, n, R,R¹ and R² are as hereinabove defined, to form a compound of formula XIII

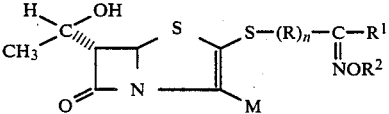

XIII wherein n, R, R¹, R² and M are as hereinabove defined.

(i) treatment of a compound of formula XIII under catalytic conditions when M is —COOCH₂CH=CH₂ to remove the allyl protecting group in the presence of an alkali base (if the product is a zwitterion, deprotection requires only the catalyst and any mild nucleophile, e.g., H₂O, alcohol, etc.) or if M is —COOCH₂CH₂R⁶, treating the compound of formula XIII with one equivalent of fluoride ion to form the compounds of formula I.

The preferred process for producing the compounds of this invention is referred to as Process C in the aforementioned patent application and comprises the steps of (a) reaction of the azetidinone of formula II in which P is hydrogen as in the following formula II(a)

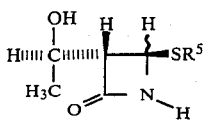 II(a)

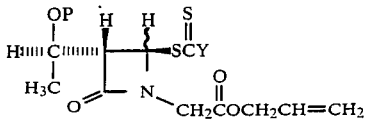 XVII wherein $R^5$ is a sulfur protecting group selected from triphenylmethyl, diphenylmethyl, 2-pyranyl, or lower alkyl carbonyl; with an [a]-substituted allyl acetate of formula XIV wherein Y and P are as hereinabove defined;

(e) treatment of compound XVII with a non-nucleophilic strong base to form a compound of formula IX(a') which is tautomeric with formula IX(b')

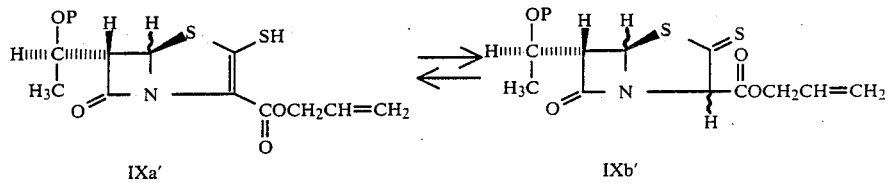

wherein P is as hereinabove defined;

(f) treatment of the tautomer of formulas IX(a') and IX(b') under conditions which effect removal of the hydroxy protecting group when P is a hydroxy protecting group.

Following steps (h) and (i) of Process A as applied to the tautomer of formulas IX(a') and IX(b') yields compounds of formula I.

In the most preferred embodiment, the substituted allyl acetate of formula XIV is added to the azetidinone of formula II(a) to form the intermediate of formula XV. The intermediate of formula XV is then utilized directly in steps (b), (c) and (d) which are conducted sequentially without isolation of any intermediates.

Likewise steps (e) and (f) are preferably conducted sequentially without the necessity of isolating any intermediates.

Step (a) involves the reaction of an azetidinone of formula II(a) at 15°-30° C. in the presence of an acid acceptor with an α-substituted allyl acetate of formula XIV to form the compound of formula XV. Preferred W leaving groups in the compound of formula XIV include tosyl, mesyl, chloro, bromo, iodo, and trifluoromethansulfonyl. Particularly preferred W leaving groups are iodo and bromo.

Where the solvent utilized is also an acid acceptor, for instance, pyridine, no additional reagent is utilized. Alternatively, an organic solvent such as acetonitrile may be employed. In these cases, a separate acid acceptor, organic or inorganic must be added to the system. Preferably, the reaction is conducted in acetonitrile employing cesium carbonate or tetra alkyl ammonium hydroxide as the acid acceptor.

Step (b) involves the conversion of the compound of formula XV to the corresponding thiol of formula XVI by deprotecting the sulfur with a stoichiometric amount of elemental zinc in hydrochloric acid. Step (c) involves the protection of the 6-hydroxy substituent to form the compound of formula XVI(a) with the preferred protecting group being trimethylsilyl, whereas step (d) is that wherein a compound of formula XVI or XVI(a) is converted to a compound of formula XVII by addition of a thiocarbonyl reagent of formula VII wherein the Y leaving group is typically imidazolyl, chloro, bromo, or iodo.

In Step (b) typically, a polar solvent such as methylene chloride, methanol, ethanol, dimethylformamide

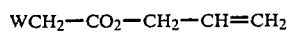 XIV wherein W is a leaving group; to form the intermediate of formula XV

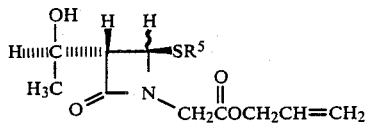 XV wherein $R^5$ is as defined hereinabove.

(b) treatment of the compound of formula XV with a stoichiometric excess of elemental zinc in a strong acid to deprotect the sulfur and form the compound of formula XVI

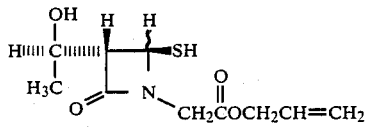 XVI (c) treatment of the compound of formula XVI with a hydroxy protecting group to form the compound of formula XVI(a)

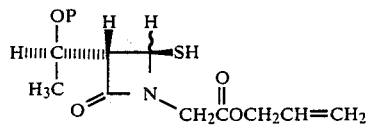 XVI(a)

wherein P is a hydroxy protecting group as hereinabove defined;

(d) reaction of the compound of formula XVI or XVI(a) with a thiocarbonyl compound of formula VII

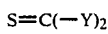 VII $$S=C(-Y)_2$$

wherein Y is a leaving group to form a compound of formula XVII (DMF), tetrahydrofuran, dimethylsulfoxide or acetonitrile is utilized. Water, or any proton source, adjusted by the addition of a strong acid, is added to enhance the activity of zinc. Typical temperatures range from −15° C. to about room temperatures (about 25° C.) with a temperature of about 0° C. being preferred. The removable hydroxy and sulfur protecting groups used are preferably those which are removable by elemental zinc. In the event a removable hydroxy protecting group is used which is not removable by zinc, a separate removal step is conducted to remove the hydroxy protecting group by means well known in the β-lactam art. This separate removal step can be conducted immediately after this step (b) or at any other time in the process after step (b).

Step (c) involves the protection of the 6-hydroxy substituent if it had not been previously protected. Hydroxy protecting groups are well known in the beta lactam art. A particularly preferred reagent for this step is bis trimethylsilylacetamide which readily forms the trimethylsilyl protecting group at the 6-hydroxy moiety. Preferably step (c) is conducted directly upon the completion of step (b) without isolation of the thiol of formula XVI. Thus the inert solvent utilized, e.g. DMF, may be the same as the one used in step (b). Solvents such as chloroform, methylene chloride and the like may also be employed in step (c). Temperatures for the reaction of step (c) range from 0° C. to 30° C.

Step (d) is wherein the intermediate of formula XVI or XVI(a) is converted to the thiocarbonyl compound of formula XVII by reaction of the compound of formula XVI or XVI(a) with the thiocarbonyl reagent of formula VII. Typically, this step (d) is conducted directly upon the completion of step (c) without isolation of the intermediate of formula XVI or XVI(a). Thus, the solvent utilized may be the same as the one used in step (c). Temperatures for the reaction of step (d) range from about 10° C.–45° C., with room temperature (about 25° C.) being generally preferred. The thiocarbonyl reagent of formula VII has the following structure $$S=C(-Y)_2 \qquad \text{VII}$$

wherein Y is a leaving group. Typical of such leaving groups are chloro, bromo, iodo, imidazolyl or aryloxy such as naphthyloxy. Preferred are 1,1′-thiocarbonyldiimidazole or beta naphthyloxythiocarbonylchloride.

Step (e) involves the cyclization of the compound of formula XVII into the thione of formula IX(a′) and IX(b′). The reaction is typically conducted in an anhydrous inert organic solvent such as tetrahydrofuran and the like. An essentially equimolar amount of a strong base such as lithium diisopropyl amide (LDA), lithium di(trimethylsilyl)amine and the like is added to the system to effect cyclization. Typically, the reaction is conducted at from −50° to −100° C., preferably at −70° C., and is generally complete from within 5 minutes to 24 hours.

Step (f) involves the removal of the 6-hydroxy protecting group in the compound of formulas IX(a′) and IX(b′) to form the compound of formulas IX(a) and IX(b).

Methods for the removal of this group are well known in the beta lactam art. Preferably, when the 6-hydroxy protecting group is trimethylsilyl, addition of a mild aqueous acid solution, such as acetic acid, to the same solution as is employed in step (e) effects removal.

The term "removable hydroxy protecting group" as used herein means any such group conventionally used for this purpose, with the only requirement being compatibility with the hydroxy substituent on the penems and removability utilizing elemental zinc or any other conventional agent for this purpose which will not adversely effect the penem structure. For the purpose of this invention, preferred hydroxy protecting groups include trichloroethoxycarbonyl, dimethyltributylsilyl, trimethylsilyloxycarbonyl and trimethylsilyl.

Step (g), is wherein the reaction of compounds of formulas IX(a) and IX(b) with compounds of formula XII is conducted in an inert atmosphere, such as nitrogen, in an organic solvent such as tetrahydrofuran (THF). The reaction is completed within 1 to 3 hours to yield allyl-2-(oximinoalkylthio)-6-(1-hydroxyethyl)-penem-3-carboxylate compounds of formula XIII.

Removal of the allyl group in Step (h) to yield the compounds of formula I is effected by the addition of the above allyl ester to a solution containing palladium (zero) and an alkali alkylcarboxylate, carboxylic acid or aqueous carbonate. This is described by McCombie in U.S. Pat. No. 4,314,942 which is incorporated herein by reference. Under these conditions, the removal of the allyl group and formation of the alkali salt or the free acid of the compound occurs.

The compounds of formula XII are either known compounds or are prepared from known compounds by conventional processes for preparing oximes by reacting the appropriate aldehyde or ketone with a hydroxyl amine or ammonium hydroxide.

Generally the process is carried out as follows:

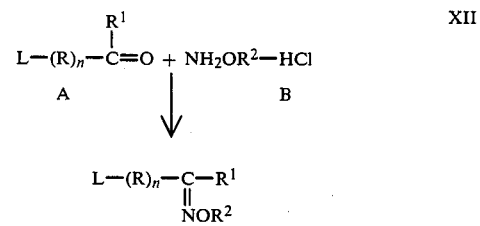

wherein L, n, R, $R^1$ and $R^2$ are as defined hereinabove.

Following the procedures of steps (g) and (h) described hereinabove, compound XII is converted to a compound of formula I.

The following examples illustrate the preparation of the compounds and compositions of this invention.

EXAMPLE 1

Preparation of allyl (5R,6S,8R)-2-thiol-6-(1-hydroxyethyl)penem-3-carboxylate and allyl (5R,6S,8R)-2-thiocarbonyl-6-(1-hydroxyethyl)penam-3-carboxylate (A) Preparation of (3S,4R)-1-(allyloxycarbonylmethyl)-3-(1-hydroxyethyl)-4-(triphenylmethylthio)azetidin-2-one Add 3 gm of (3S,4R)-3-(1-hydroxyethyl)-4-(triphenylmethylthio)azetidin-2-one to 10 ml of acetonitrile containing 0.286 gm of cesium carbonate. Add 0.2 gm of alpha-iodo allyl acetate to the system. Stir the system at room temperature for 16 hours. Dilute with ether (50 ml), filter and wash the ether layer with 1% aqueous phosphoric acid, followed by water. After drying over sodium sulfate remove solvent to give a foamy solid.

(B) Preparation of (3S,4R)-3-(1-hydroxyethyl)-1-allyloxycarbonylmethyl-4-sulfhydryl-azetidin-2-one Add 500 mg of (3S,4R)-1-(allyloxycarbonylmethyl)-3-(1-hydroxyethyl)-4-triphenylmethylthio)azetidin-2-one and 20 ml tetrahydrofuran to a 50 ml flask. Add zinc dust and 10% hydrochloric acid in small portions over 1 hour until all of the starting material is reacted. Recover the product by filtering off the excess zinc and removing the solvent to crystallize the title product.

NMR: (CDCl$_3$)=6.2–5.7(1H, m); 5.5–5.15 (2H, m); 5.0 (1H, dd, J=3,9 c/s); 4.75–4.55 (2H,m); 4.45–3.95 (1H,m); 4.14(1H, d, J=18 c/s); 3.78(1H, d, J=18 c/s); 3.19(1H, dd, J=6,3 c/s); 2.09(1H, d, J=9 c/s); 1.34(3H, d, J=6 c/s).

(C) Preparation of (3S,4R)-3-(1-trimethylsilyloxy-ethyl-1-allyloxycarbonylmethyl-4-sulfhydryl-azetidin-2-one Add the entire amount of (3S,4R)-3-(1-hydroxyethyl)-1-allyloxycarbonylmethyl-4-sulfhydryl-azetidin-2-one produced in step (B) above to 25 ml of methylene chloride. To this system add 1.1 ml of bis silylacetamide. Stir the system at room temperature for 15 minutes to give the title compound.

(D) Preparation of (3S,4R)-1-(allyloxycarbonylmethyl)-3-(1-trimethyl-silyloxyethyl)-4-(1'-imidazolylthiocarbonylthio)azetidin-2-one After completion of step (C) above and to the same solution add 350 mg of thiocarbonyldiimidazole. Stir the system at room temperature for 3 hours. Filter the solution and wash the precipitate with methylene chloride. Collect the filtrate and remove the methylene chloride by stripping. Chromatograph the residue on silica gel eluting with 20% ethyl acetate/methylene chloride to yield 335 mg of the title compound.

NMR: =8.4, 1H, s; 7.65, 1H, d(J=1 Hz); 7.05, 1H (dJ=Hz); 5.95, 1H, d (J=2 Hz); 5.8, 1H,m; 5.45–5.1, 2H, m; 4.3, 1H, m; 4.1, 2H, Q(J=16 Hz); 3.5, d,d (J=2,6); 1.35; 3H, d (J=6 Hz).

(E) Preparation of (5R,6S,8R)allyl-2-thiol-6-(1-trimethylsilyloxyethyl)-penem-3-carboxylate and (5R,6S,8R)allyl-2-thiocarbonyl-6-(1-trimethylsilyloxyethyl)penam-3-carboxylate Add 170 mg of (3S,4R)-1-(allyloxycarbonylmethyl)-3-(1-trimethylsilyloxyethyl)-4-(1'-imidazolylthiocarbonylthio)azetidin-2-one to 40 ml of anhydrous tetrahydrofuran under a nitrogen atmosphere. Cool the system to −78° C. and then add 0.6 ml of 1M lithium di(trimethylsilyl)amine in hexane dropwise to the system. Stir the system at −78° C. for 5 minutes. Add 0.2 ml of acetic acid to the system. Dilute the system to 200 ml with methylene chloride. Wash the organic solution with water, aqueous sodium bicarbonate solution and again with water. Purify the product by chromatography by rapidly eluting the sample through silica gel with 5% ethyl acetate/methylene chloride to afford 125 mg of the desired products and the desilylated products.

(F) Preparation of (5R,6S,8R)allyl-2-thiol-6-(1-hydroxyethyl)penem-3-carboxylate and (5R,6S,8R)allyl-2-thiocarbonyl-6-(1-hydroxyethyl)penam-3-carboxylate To a 25 ml flask add the entire mixture produced in step (E) along with 5 ml of tetrahydrofuran, 1 ml of water and 1 ml of acetic acid. Stir the system at room temperature for 2 hours. Add ethyl acetate to the solution and wash the organic phase with sodium bicarbonate solution, water and then brine. Dry the organic phase over anhydrous sodium sulfate, filter and remove the solvent by stripping to give the title compound.

EXAMPLE 2

(A) (5R,6S,8R)Allyl-2-oximino-3-propylthio)-6-(1-hydroxyethyl)penem-3-carboxylate Dissolve 200 mg of the compound prepared in Example 1 in 5 ml tetrahydrofuran (THF). Add 20 drops of 5% NaHCO$_3$, then add 300 microliters α-bromo acetone oxime. The reaction was completed in about 30 minutes to yield the title allyl ester.

(B) (5R,6S,8R)2-(2-oximino-3-propylthio)-6-(1-hydroxyethyl)penem-3-carboxylic acid Add about 700 mg of the compound produced in part A of this Example 2 in a mixture of 10 ml CH$_3$CN, 2 ml water containing 250 mg pyridine and 5 ml CH$_2$Cl$_2$ into 200 mg triphenylphosphine and 100 mgs Pd° reagent and stir for about 3 hours, at which time the reaction is complete as shown by TLC and reverse phase TLC. The product was eluted with water to yield the title carboxylic acid.

90 mHz NMR in CDCl$_3$, 1.3 ppm, D J=6 Hz, 3H, 1.95 ppm, s, 3H, 3.75 ppm, m, 2H, 4–4.4 ppm m, 1H, 4.5–4.8 ppm, m, 2H, 5.1–5.5 ppm, m, 2H, 5.6 ppm broad S, 1H, 5.6–6.1 ppm, m, 1H.

EXAMPLE 3

(A) (5R,6S,8R)Allyl-2-(2-oximino-1-ethylthio)-6-(1-hydroxyethyl)penem-3-carboxylate React 2.5 gm Cl—CH$_2$CHO in aqueous solution with 1.2 equivalents of NH$_3$OHCl in aqueous solution. Neutralize the resulting acidic solution with NaHCO$_3$ to about pH 8, saturate with sodium chloride and extract with ether to yield Cl—CH$_2$—CH=N   OH.

Add 200 μl Cl—CH$_2$—CH=N   OH neat to about 600 mg of the product of Example 1 in 25 ml THF, 0.7 gram NaHCO$_3$ (4 equivalents) and 25 ml water. The reaction is complete in about 30 seconds to yield the title allyl ester.

90 mHz NMR in CDCl$_3$, 1.2 ppm, D J=6 Hz, 3H, 3.5–3.8 ppm, 3H, 4–4.3 ppm, m, 1H, 4.5–4.7 ppm, m, 2H, 5.0–5.5 ppm, m, 2H, 5.55 ppm, broad 5, 1H, 5.55–6.1, m, 1H, 6.8 and 7.35 ppm, 2 triplets, J=6 Hz—Isomeric oxime.

(B) (5R,6S,8R)sodium-2-(2-oximino-1-ethylthio)-6-(1-hydroxyethyl)penem-3-carboxylate Make a reaction mixture of 300 mg of the allyl ester prepared in this Example 3A, 20 ml of a 50/50 volume mixture of CH$_3$CN and CH$_2$Cl$_2$, 3 ml isopropylalcohol, 100 mg Pd° reagent and 300 mg of triphenylphosphine. The reaction is complete in 45 minutes. Add 30 ml H$_2$O, 1 equivalent NaHCO$_3$ and remove the solvent to give the title compound.

EXAMPLE 4

(A)

(5R,6S,8R)Allyl-2-(2-methoxyimino-1-ethylthio)-6-(1-hydroxyethyl)penem-3-carboxylate Mix about 10 gm of Cl—CH$_2$CH=O in 25 ml water and 10 gm C$_3$O—NH$_3$Cl in 25 ml water and adjust the pH of the reaction mixture to about pH 7. Extract with ether/ethyl acetate. The NMR indicates both oxime isomers of Cl—CH$_2$CH=N   OCH$_3$.

To a mixture of 500 mg of the thione prepared in Example 1 in 25 ml THF, 600 mg (4 equivalents) NaHCO$_3$ and 25 ml water add Cl—CH$_2$CH=N   OCH$_3$ in portions until thin layer chromatography (TLC) shows no thione remaining. Filter and remove the solvent to give the title allyl ester.

(B)

(5R,6S,8R)Sodium-2-(2-methoxyimino-1-ethylthio)-6-(1-hydroxyethyl)penem-3-carboxylate To the allyl ester of this Example 4A add 20 ml. CH$_3$CN/CH$_2$Cl$_2$ (50/50), 3 ml isopropyl alcohol, 100 mg Pd° reagent and 300 mg triphenyl phosphine which results in removal of the allyl group in about one hour. To the deprotected compound add 30 ml water and 1 equivalent NaHCO$_3$ then remove the solvent and recover the title compound.

90 mHz NMR sodium salt in D$_2$O, 1.15 ppm, D J=6 Hz, 3H, 3.5 ppm DD J=3,6 Hz, 3.7 ppm, S, 3H, 3.6–3.8 ppm, m, 2H, 4.0–4.3 ppm, m, 1H, 5.5 ppm, S, 1H, 6.85 and 7.40 ppm 2 triplets J=6 Hz—Isomeric Oxime.

EXAMPLE 5

(A)

(5R,6S,8R)Allyl-2-(3-oximinobutylthio)-6-(1-hydroxyethyl)penem-3-carboxylate

Add 8.0 gm HONH$_3$Cl in 25 ml water to 7.0 grams $$CH_2=CH-\underset{\underset{O}{\|}}{C}-CH_3$$

in 100 ml water, adjust the resulting pH of about 1 to pH 6.0 with 8.4 gm NaHCO$_3$ added portionwise. Saturate with NaCl and extract with ether. Remove the solvent to recover a mixture of two isomeric oximes (shown by NMR).

To 600 mg of the thione (prepared in Example 1) in 20 ml of THF and about 6 equivalents of the oximes $$CH_2=CH-\underset{\underset{N\sim OH}{\|}}{C}-CH_3$$

neat and leave overnight at room temperature. Drive the reaction to completion by removing the THF solvent to yield the title allyl ester.

(B)

(5R,6S,8R)sodium-2-(3-oximinobutylthio)-6-(1-hydroxyethyl)penem-3-carboxylate

The product of this Example 5A is deprotected by mixing it with CH$_3$CN/H$_2$O/CH$_2$Cl$_2$ in a volume ratio of 45/10/45, the Pd° reagent and triphenyl phosphine. The reaction is complete in about 2 hours. The product is extracted with water/CH$_2$Cl$_2$ (50/50) and 100 mg NaHCO$_3$ is added to yield the title compound.

90 mHz NMR Na in D$_2$O, 1.2 ppm, D J=6 Hz, 3H, 1.8 ppm,s, 3H, 2.4–2.8 ppm, m,2H, 2.8–3.2 ppm, m, 2H, 3.75 ppm, DD J=1, 6 Hz, 1H, 4.1 ppm, m, 1H, 5.55, D J=1 Hz, 1H.

Following the procedures of the preceding examples using analogous reagents which are known or which can be prepared by methods known in the art for preparing analogous compounds, the following are prepared

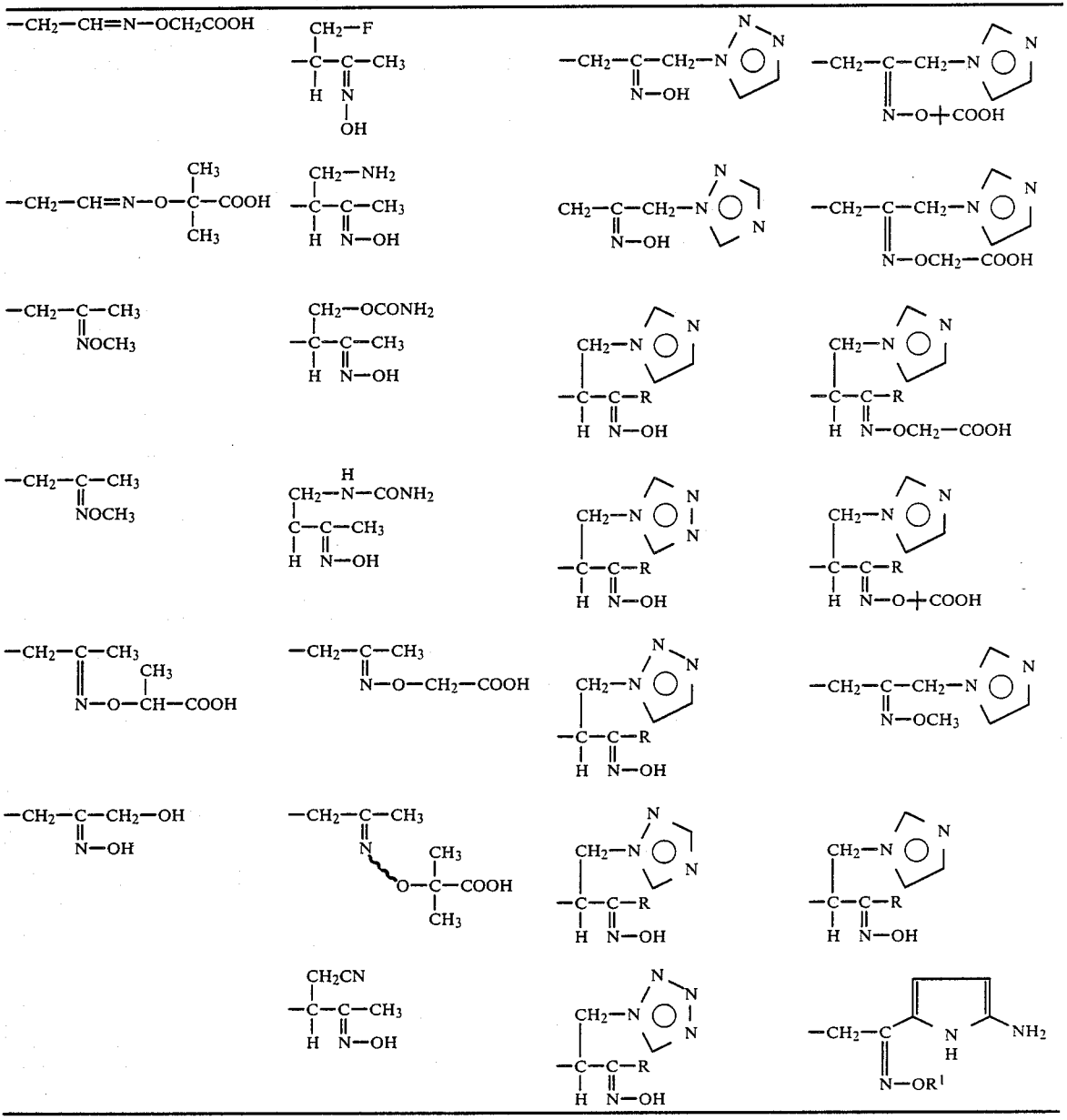

In the following examples, the Active Ingredient is 5R,6S,8R-2-(2-oximino-3-propylthio)-6-(1-hydroxyethyl)penem-3-carboxylic acid;
5R,6S,8R-2-(2-oximino-1-ethylthio)-6-(1-hydroxyethyl)penem-3-carboxylic acid;
5R,6S,8R-2-(2-methoxyimino-1-ethylthio)-6-(1-hydroxyethyl)penem-3-carboxylic acid; or
5R,6S,8R-2-(3-oximinobutylthio)-6-(1-hydroxyethyl)penem-3-carboxylic acid; or equivalent amount of a penem of a compound of formula I.

EXAMPLE 6

Capsules

| No. | Ingredient | mg/tablet | mg/tablet |
|---|---|---|---|
| 1. | Active Ingredient | 250 | 500 |
| 2. | Lactose USP | 100 | 50 |
| 3. | Corn Starch, Food Grade | 50 | 43.5 |
| 4. | Microcrystalline Cellulose NF | 95 | 50 |

| No. | Ingredient | mg/tablet | mg/tablet |
|---|---|---|---|
| 5. | Magnesium Stearate NF | 5 | 6.5 |
|  | Total | 500 | 650 |

Method of Manufacture

Mix Items Nos. 1, 2, 3 and 4 in a suitable mixer for 10–15 minutes. Add Item No. 5 and mix for 1–3 minutes. Fill the mixture into suitable two-piece hard gelatin capsules using encapsulating machine.

EXAMPLE 7

Tablets

| No. | Ingredient | mg/tablet | mg/tablet |
|---|---|---|---|
| 1. | Active Ingredient | 250 | 500 |
| 2. | Lactose USP | 57 | 114 |
| 3. | Corn Starch, Food Grade 10% paste in Purified Water | 20 | 40 |
| 4. | Corn Starch, Food Grade | 18 | 39 |
| 5. | Magnesium Stearate NF | 5 | 7 |
|  | Total | 350 | 700 |

Method of Manufacture

Mix Item Nos. 1 and 2 in a suitable mixer for 10–15 minutes. Granulate the mixture with Item No. 3. Past the wet granulation through a coarse screen (e.g., ¼″) if needed, and dry the wet granules. Mill the dried granules. Combine Item No. 4 and the dried granules and mix for 10–15 minutes. Add Item No. 5 and mix for 1–3 minutes. Compress the mixture to appropriate size and weight on a suitable tablet machine.

EXAMPLE 8

Injectable Powder: (per vial)

|  | g/vial | g/vial |
|---|---|---|
| Active Ingredient | 0.5 | 1.0 |

Add sterile water for injection or bacteriostatic water for injection for reconstitution

EXAMPLE 9

Injectable Solution

| Ingredient | mg/ml | mg/ml |
|---|---|---|
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 1.5 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°–70° C.
2. Cool to 25°–35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22 micron membrane and fill into appropriate containers.
6. Terminally sterilize the units by autoclaving.

EXAMPLE 10

Injectable Powder: (per vial)

|  | g/vial |
|---|---|
| Active Ingredient | 1.0 |
| Sodium Citrate | 0.05 | pH is adjusted to 6.2 using 0.1N citric acid solution.

Add sterile water for injection or bacteriostatic water for injection for reconstitution.

We claim:

1. Compounds represented by the formula

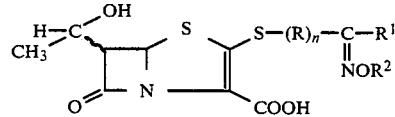

and pharmaceutically acceptable salts and pharmaceutically acceptable esters thereof, in racemic or optically active forms,
wherein
n is one or two;
R represents

wherein $R^3$ and $R^4$ are independently selected from hydrogen, lower alkyl, hydroxy-lower alkyl, halo-lower alkyl, amino-lower alkyl, carbamido-lower alkyl, cyano-lower alkyl, carbamoyloxy-lower alkyl, carbamoyl-lower alkyl, carboxy-lower alkyl, heterocyclyl-lower alkyl wherein the heterocyclic moiety has 5 or 6 ring atoms, at least one of which is carbon, and the remaining 4 or 5 ring atoms are independently selected from carbon, nitrogen, oxygen and sulfur; or $R^3$ and $R^4$ taken together are =O;

$R^1$ represents hydrogen, lower alkyl, hydroxy-lower alkyl, amino-lower alkyl, carboxy-lower alkyl, carbamoyloxy-lower alkyl, carbamoyl-lower alkyl, haloloweralkyl, cyano-lower alkyl, heterocyclyl lower alkyl wherein the heterocyclic moiety has 5 or 6 ring atoms, at least one of which is carbon, and the remaining ring atoms are independently selected from oxygen, carbon, nitrogen and sulfur;

$R^2$ represents hydrogen, lower alkyl, carboxy-lower-alkyl, hydroxy-lower alkyl, cyano-lower alkyl, amino-lower alkyl, imidazolyl-lower alkyl, triazolyl-lower alkyl, tetrazolyl-lower alkyl or pyridinium-lower alkyl.

2. Compounds of claim 1 wherein $R^1$ and $R^2$ are each independently hydrogen or lower alkyl, and $R^3$ and $R^4$ are each hydrogen.

3. Compounds of claim 1 wherein n is one, $R^2$, $R^3$ and $R^4$ are each hydrogen and $R^1$ is hydrogen or methyl.

4. A compound of claim 1 which is (5R,6S,8R)2-(2-oximino-3-propylthio)-6-(1-hydroxyethyl)penem-3-carboxylic acid.

5. A compound of claim 1 which is (5R,6S,8R)2-(2-oximino-1-ethylthio)-6-(1-hydroxyethyl)-penem-3-carboxylic acid.

6. A compound of claim 1 which is (5R,6S,8R)2-(2-methoxyimino-1-ethylthio)-6-(1-hydroxyethyl)penem-3-carboxylic acid.

7. A compound of claim 1 which is (5R,6S,8R)2-(3-oximinobutylthio)-6-(1-hydroxyethyl)penem-3-carboxylic acid.

8. A pharmaceutical composition comprising an antibacterial effective amount of a compound of claim 1 in admixture with a pharmaceutically acceptable carrier therefor.

9. A composition according to claim 8 wherein said antibacterial compound is (5R,6S,8R)2-(2-oximino-3-propylthio)-6-(1-hydroxyethyl)penem-3-carboxylic acid.

10. A composition according to claim 8 wherein said antibacterial compound is (5R,6S,8R)2-(2-oximino-1-ethylthio)-6-(1-hydroxyethyl)penem-3-carboxylic acid.

11. A composition according to claim 8 wherein said antibacterial compound is (5R,6S,8R)2-(2-methoxyimino-1-ethylthio)-6-(1-hydroxyethyl)penem-3-carboxylic acid.

12. A composition according to claim 8 wherein said antibacterial compound is (5R,6S,8R)-2-(3-oximinobutylthio)-6-(1-hydroxyethyl)penem-3-carboxylic acid.

13. A method of preventing bacterial infections in patients in need of such treatment which comprises administering an antibacterial effective amount of a compound of claim 1.

14. The method of claim 13 wherein the compound administered is (5R,6S,8R)2-(2-oximino-3-propylthio)-6-(1-hydroxyethyl)penem-3-carboxylic acid.

15. The method of claim 13 wherein the compound administered is (5R,6S,8R)2-(2-oximino-1-ethylthio)-6-(1-hydroxyethyl)penem-3-carboxylic acid.

16. The method of claim 13 wherein the compound administered is (5R,6S,8R)2-(2-methoxyimino-1-ethylthio)-6-(1-hydroxyethyl)penem-3-carboxylic acid.

17. The method of claim 13 wherein the compound administered is (5R,6S,8R)2-(3-oximinobutylthio)-6-(1-hydroxyethyl)penem-3-carboxylic acid.

* * * * *